US00PP20576P2

(12) United States Plant Patent
Hofmann

(10) Patent No.: US PP20,576 P2
(45) Date of Patent: Dec. 15, 2009

(54) ***BEGONIA* PLANT NAMED 'INNBOLORA'**

(50) Latin Name: *Begonia hybrida*
Varietal Denomination: Innbolora

(75) Inventor: Silvia Hofmann, Mainz (DE)

(73) Assignee: Innovaplant GmbH + Co. KG, Gensingen (DE)

( * ) Notice: Subject to any disclaimer, the term of this patent is extended or adjusted under 35 U.S.C. 154(b) by 0 days.

(21) Appl. No.: 12/286,069

(22) Filed: Sep. 26, 2008

(51) Int. Cl.
*A01H 5/00* (2006.01)

(52) U.S. Cl. ..... Plt./347

(58) Field of Classification Search ..... Plt./347

See application file for complete search history.

*Primary Examiner*—Kent L Bell
(74) *Attorney, Agent, or Firm*—C. A. Whealy

(57) ABSTRACT

A new and distinct cultivar of *Begonia* plant named 'Innbolora', characterized by its compact and mounded to trailing plant habit; freely branching habit; dense and bushy growth habit; dark green-colored leaves; and numerous single flowers that are bright orange in color.

1 Drawing Sheet

Botanical designation: *Begonia hybrida.*
Cultivar denomination: 'Innbolora'.

BACKGROUND OF THE INVENTION

The present invention relates to a new and distinct cultivar of *Begonia* plant, botanically known as *Begonia hybrida* and hereinafter referred to by the name 'Innbolora'.

The new *Begonia* plant is a product of a planned breeding program conducted by the Inventor in Gensingen, Germany. The objective of the breeding program was to develop new compact *Begonia* cultivars with attractive single flowers.

The new *Begonia* plant originated from a cross-pollination made by the Inventor in September, 2003 of *Begonia×tuberhybrida* 'Elserta', not patented, as the female, or seed, parent with an unnamed selection of *Begonia boliviensis*, not patented, as the male, or pollen, parent. The new *Begonia* was discovered and selected by the Inventor as a single plant from within the progeny of the stated cross-pollination in a controlled greenhouse environment in Gensingen, Germany in September, 2004.

Asexual reproduction of the new *Begonia* plant by vegetative cuttings in a controlled greenhouse environment in Gensingen, Germany since October, 2004, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Innbolora'. These characteristics in combination distinguish 'Innbolora' as a new and distinct cultivar of *Begonia:*

1. Compact and mounded to trailing plant habit.
2. Freely branching habit; dense and bushy growth habit.
3. Dark green-colored leaves.
4. Numerous single flowers that are bright orange in color.

Plants of the new *Begonia* differ from plants of the female parent, 'Elserta', primarily in flower form as plants of 'Elserta' have double flowers.

Plants of the new *Begonia* differ from plants of the male parent selection in the following characteristics:

1. Plants of the new *Begonia* are more compact than and not as trailing as plants of the male parent selection.
2. Plants of the new *Begonia* are more freely branching than plants of the male parent selection.
3. Plants of the new *Begonia* have larger flowers than plants of the male parent selection.

Plants of the new *Begonia* can also be compared to plants of the *Begonia×tuberhybrida* 'Bonfire', disclosed in U.S. Plant Pat. No. 15,108. In side-by-side comparisons conducted in Gensingen, Germany, plants of the new *Begonia* differed from plants of 'Bonfire' in the following characteristics:

1. Plants of the new *Begonia* were more compact and mounded than plants of 'Bonfire'.
2. Plants of the new *Begonia* were more freely branching and denser than plants of 'Bonfire'.

BRIEF DESCRIPTION OF THE PHOTOGRAPHS

The accompanying colored photographs illustrate the overall appearance of the new *Begonia*, showing the colors as true as it is reasonably possible to obtain in colored reproductions of this type. Colors in the photographs may differ slightly from the color values cited in the detailed botanical description which accurately describe the colors of the new *Begonia* plant.

The photograph at the bottom of the sheet comprises a side perspective view of a typical flowering plant of 'Innbolora' grown in a container.

The photograph at the top of the sheet is a close-up view of typical flowers and leaves of 'Innbolora'.

DETAILED BOTANICAL DESCRIPTIONS

Plants used for the aforementioned photographs and following observations and measurements were grown in Bonsall, Calif. in one-gallon containers and under commercial practice in a shaded polyethylene-covered greenhouse during the late summer. During the production of the plants, day temperatures ranged from 18° C. to 35° C., night temperatures ranged from 10° C. to 24° C. Plants used for the photographs and the description were pinched one time and were twelve weeks from planting. In the following description, color references are made to The Royal Horticultural Society Colour Chart, 2001 Edition, except where general terms of ordinary dictionary significance are used.

Botanical classification: *Begonia hybrida* 'Innbolora'.

Parentage:

*Female, or seed, parent.*—*Begonia×tuberhybrida* 'Elserta', not patented.

*Male, or pollen, parent.*—Unnamed selection of *Begonia boliviensis*, not patented.

Propagation:

*Type.*—By vegetative cuttings.

*Time to initiate roots, summer.*—About 7 to 10 days at temperatures of about 18° C. to 24° C.

*Time to initiate roots, winter.*—About 9 to 14 days at temperatures of about 18° C. to 24° C.

*Time to produce a rooted young plant, summer.*—About four weeks at temperatures of about 18° C. to 24° C.

*Time to produce a rooted young plant, winter.*—About five weeks at temperatures of about 18° C. to 24° C.

*Root description.*—Fine, fibrous; white in color. Plants of the new *Begonia* have not been observed to form tubers.

*Rooting habit.*—Moderate branching; moderately dense.

Plant description:

*Plant and growth habit.*—Compact and mounded to trailing plant habit; freely branching with about six to seven branches per plant; dense and bushy growth habit; vigorous growth habit.

*Plant height.*—About 22 cm.

*Plant width.*—About 24 cm by 26 cm.

*Branch description.*—Length: About 20 cm. Diameter: About 7 mm. Internode length: About 3.2 cm. Texture: Smooth, glabrous. Color: Close to 197A tinted with close to 183D.

*Leaf description.*—Arrangement: Alternate; simple. Length: About 13.6 cm. Width: About 4.2 cm. Shape: Lanceolate; asymmetrical. Apex: Acute. Base: Oblique. Margin: Bi-serrate. Texture, upper and lower surfaces: Smooth, glabrous. Venation pattern: Palmate; reticulate. Color: Developing leaves, upper surface: Close to 137A. Developing leaves, lower surface: Close to 148B. Fully expanded leaves, upper surface: Close to N137D; at the margins, close to 183B; venation, close to 137A. Fully expanded leaves, lower surface: Close to 147B; venation, close to 147B. Petiole length: About 4.3 cm. Petiole diameter: About 3 mm. Petiole texture, upper and lower surfaces: Sparsely pubescent. Petiole color, upper and lower surfaces: Close to 199B.

Flower description:

*Flowering habit.*—Actinomorphic single flowers; flowers axillary in clusters of typically three; staminate and pistillate flowers observed. Freely flowering habit with about five to seven flowers and flower buds per lateral branch. Flowers drooping.

*Fragrance.*—None detected.

*Natural flowering season.*—Plants flower continuously from April to October in Germany. Flowers last about two to three days on the plant; flowers not persistent.

*Flower buds.*—Shape: Elliptic. Length: About 2.4 cm. Diameter: About 1.2 cm. Color: Close to N34B.

*Flowers, staminate flowers.*—Diameter: About 4.4 cm. Depth (height): About 3 cm.

*Flowers, pistillate flowers.*—Diameter: About 2.4 cm. Depth (height): About 3.4 cm.

*Tepals, staminate flowers.*—Quantity/arrangement: Four in a single whorl. Length: About 3.3 cm to 3.5 cm. Width: About 6 mm to 11 mm. Shape: Elliptic to narrowly elliptic. Apex: Acute. Base: Rounded to truncate. Margin: Entire. Texture, upper and lower surfaces: Smooth, glabrous; velvety. Color: When opening, upper and lower surfaces: Close to 34B. Fully opened, upper and lower surfaces: Close to 34A; color does not fade with development.

*Tepals, pistillate flowers.*—Quantity/arrangement: Six in a single whorl. Length: About 2.3 cm to 2.5 cm. Width: About 7 mm to 10 mm. Shape: Elliptic to narrowly elliptic. Apex: Acute. Base: Rounded to truncate. Margin: Entire. Texture, upper and lower surfaces: Smooth, glabrous; velvety. Color: When opening, upper and lower surfaces: Close to 34B. Fully opened, upper and lower surfaces: Close to 34A; color does not fade with development.

*Flower bracts.*—None observed.

*Peduncles.*—Angle: About 30° to 45° from the stem axis. Length: About 1.2 cm to 1.5 cm. Diameter: About 1 mm. Texture: Smooth, glabrous. Color: Close to 182A.

*Reproductive organs.*—Stamens (present on staminate flowers only): Quantity per flower: About 46. Filament length: About 2 mm. Filament color: Close to 155B. Anther shape: Oval. Anther length: About 2 mm. Anther color: Close to 12A. Pollen amount: Moderate. Pollen color: Close to 12B. Pistils (present on pistillate flowers only): Pistil length: About 2 cm. Stigmas per flower: Six. Stigma color: Close to 22A. Style length: About 2.5 mm. Style color: Close to 32C. Ovary color: Close to N34C.

*Seed/fruit.*—Seed and fruit production have not been observed.

Disease/pest resistance: Plants of the new *Begonia* not been observed to be resistant to pathogens and pests common to *Begonia*.

Temperature tolerance: Plants of the new *Begonia* have been observed to tolerate temperatures from about 5° C. to about 35° C.

It is claimed:

1. A new and distinct *Begonia* plant named 'Innbolora' as illustrated and described.

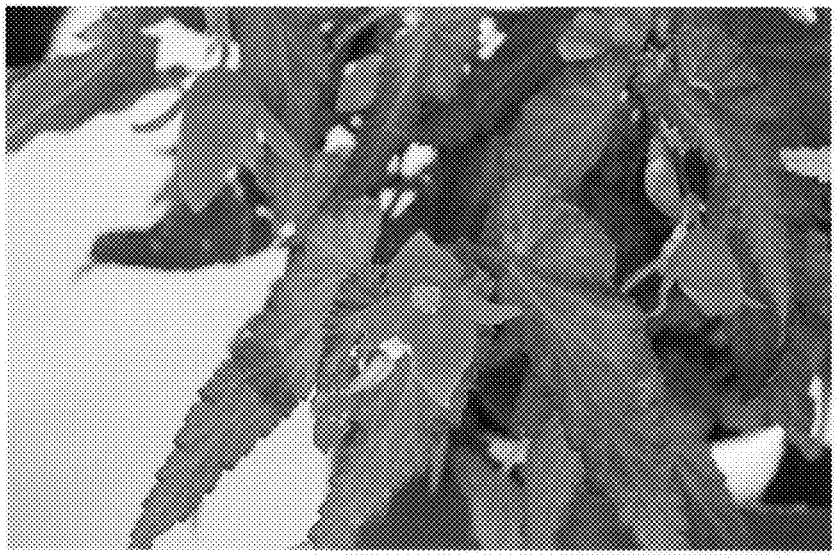
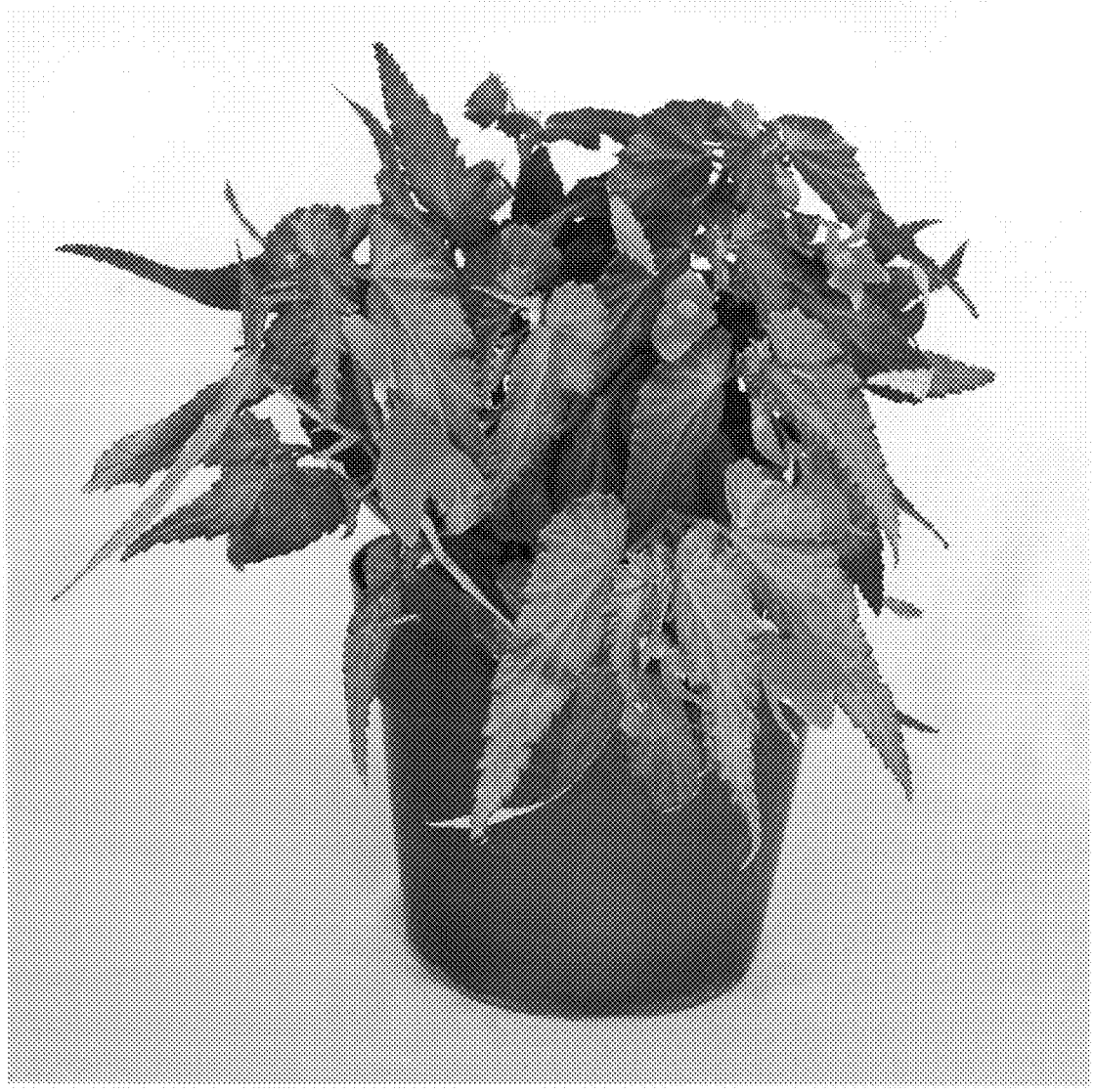

* * * * *